US008377896B2

(12) United States Patent
Migawa et al.

(10) Patent No.: US 8,377,896 B2
(45) Date of Patent: Feb. 19, 2013

(54) ANTIBACTERIAL 4,6-SUBSTITUTED 6', 6" AND 1 MODIFIED AMINOGLYCOSIDE ANALOGS

(75) Inventors: Michael T. Migawa, Carlsbad, CA (US);
Xiaojing Wang, Foster City, CA (US);
Eric E. Swayze, Encinitas, CA (US);
Richard H. Griffey, Vista, CA (US)

(73) Assignee: Isis Pharmaceuticals, Inc, Carlsbad, CA (US)

( * ) Notice: Subject to any disclaimer, the term of this patent is extended or adjusted under 35 U.S.C. 154(b) by 0 days.

(21) Appl. No.: 13/044,226

(22) Filed: Mar. 9, 2011

(65) Prior Publication Data
US 2011/0245476 A1 Oct. 6, 2011

Related U.S. Application Data

(63) Continuation of application No. PCT/US2009/056391, filed on Sep. 9, 2009.

(60) Provisional application No. 61/095,670, filed on Sep. 10, 2008.

(51) Int. Cl.
*A61K 31/70* (2006.01)
*C07H 15/20* (2006.01)
(52) U.S. Cl. .......................... 514/41; 536/13.7; 536/13.8
(58) Field of Classification Search .................. 536/13.8, 536/13.7; 514/41
See application file for complete search history.

(56) References Cited

U.S. PATENT DOCUMENTS

| | | | | |
|---|---|---|---|---|
| 3,808,198 | A | 4/1974 | Naito et al. | 260/210 AB |
| 3,860,574 | A | 1/1975 | Naito et al. | 260/210 NE |
| 3,896,106 | A | 7/1975 | Naito et al. | 260/210 AB |
| 3,897,412 | A | 7/1975 | Naito et al. | 260/210 AB |
| 3,956,274 | A | 5/1976 | Umezawa et al. | 260/210 AB |
| 4,021,601 | A | 5/1977 | Arcamone et al. | 536/17 |
| 4,066,753 | A | 1/1978 | Hanessian | 424/181 |
| 4,078,138 | A | 3/1978 | Akita et al. | 536/10 |
| 4,170,642 | A | 10/1979 | Umezawa et al. | 424/180 |
| 4,247,687 | A | 1/1981 | Hanessian | 536/12 |
| 4,337,248 | A | 6/1982 | Battistini et al. | 424/180 |
| 4,347,354 | A | 8/1982 | Cron et al. | 536/10 |
| 4,424,343 | A | 1/1984 | Cron et al. | 536/13.8 |
| 4,617,293 | A | 10/1986 | Wahlig et al. | 514/41 |
| 4,937,257 | A | 6/1990 | Gericke et al. | 514/456 |
| 5,470,836 | A | 11/1995 | Donno et al. | 514/38 |
| 5,534,408 | A | 7/1996 | Green et al. | 435/5 |
| 5,763,587 | A | * 6/1998 | Mangia | 536/13.8 |
| 5,935,776 | A | 8/1999 | Green et al. | 435/5 |
| 5,942,547 | A | 8/1999 | Gustafson et al. | 514/616 |
| 6,140,361 | A | 10/2000 | Gustafson et al. | 514/488 |
| 6,541,456 | B1 | 4/2003 | Swayze et al. | 514/38 |
| 6,759,523 | B2 | 7/2004 | Swayze et al. | 536/13.2 |
| 6,967,242 | B2 | 11/2005 | Swayze et al. | 536/13.2 |
| 7,893,039 | B2 | 2/2011 | Swayze et al. | 514/54 |
| 8,114,856 | B2 | 2/2012 | Swayze et al. | |
| 2004/0229265 | A1 | 11/2004 | Lapidot et al. | 435/6 |
| 2005/0004052 | A1 | 1/2005 | Baasov et al. | 514/39 |
| 2005/0148522 | A1 | 7/2005 | Baasov et al. | 514/36 |
| 2008/0045468 | A1 | 2/2008 | Hanessian et al. | 514/39 |
| 2008/0214845 | A1 | 9/2008 | Migawa et al. | 549/415 |
| 2008/0293649 | A1 | 11/2008 | Swayze et al. | 514/39 |
| 2008/0300199 | A1 | 12/2008 | Linsell et al. | 514/38 |
| 2010/0099661 | A1 | 4/2010 | Aggen et al. | |
| 2011/0166334 | A1 | 7/2011 | Swayze et al. | |
| 2011/0275586 | A1 | 11/2011 | Aggen et al. | |
| 2011/0288041 | A1 | 11/2011 | Aggen et al. | |
| 2012/0122809 | A1 | 5/2012 | Goldblum et al. | |
| 2012/0135945 | A1 | 5/2012 | Dozzo et al. | |
| 2012/0135946 | A1 | 5/2012 | Goldblum et al. | |
| 2012/0135948 | A1 | 5/2012 | Goldblum et al. | |
| 2012/0165282 | A1 | 6/2012 | Dozzo et al. | |
| 2012/0172332 | A1 | 7/2012 | Aggen et al. | |
| 2012/0184501 | A1 | 7/2012 | Dozzo et al. | |
| 2012/0196791 | A1 | 8/2012 | Armstrong et al. | |
| 2012/0208781 | A1 | 8/2012 | Bruss et al. | |
| 2012/0214759 | A1 | 8/2012 | Bruss et al. | |
| 2012/0214760 | A1 | 8/2012 | Bruss et al. | |

FOREIGN PATENT DOCUMENTS

| | | |
|---|---|---|
| CA | 1 271 744 | 7/1990 |
| DE | 25 15 629 A1 | 10/1975 |
| DE | 29 36 120 A1 | 3/1980 |
| DE | 30 44 970 A1 | 9/1981 |
| DE | 34 05 326 A1 | 8/1985 |
| EP | 0 021 150 A1 | 1/1981 |
| FR | 1361393 | 4/1964 |
| FR | 2183236 | 12/1973 |
| GB | 1 400 676 | 7/1975 |
| GB | 1 456 674 | 11/1976 |
| GB | 1 488 420 | 10/1977 |
| GB | 2 068 366 A | 8/1981 |
| GB | 1 600 457 | 10/1981 |
| JP | 49-92044 | 9/1974 |
| JP | 49-101355 | 9/1974 |
| JP | 52-100464 | 8/1977 |
| JP | 55-15445 A | 2/1980 |
| JP | 56-110697 | 9/1981 |
| WO | WO 82/00464 A1 | 2/1982 |
| WO | WO 92/02530 A1 | 2/1992 |
| WO | WO 94/09792 A1 | 5/1994 |
| WO | WO 00/39139 A1 | 7/2000 |
| WO | WO 01/54691 A1 | 8/2001 |

(Continued)

OTHER PUBLICATIONS

Alper et al., "Metal Catalyzed Diazo Transfer for the Synthesis of Azides From Amines," *Tetrahedron Letters* 37(34):6029-6032, 1996.
Alper et al., "Probing the Specificity of Aminoglycoside—Ribosomal RNA Interactions with Designed Synthetic Analogs," *J. Am. Chem. Soc.* 120(9):1965-1978, 1998.
Battistini et al., "Semisynthetic Aminoglycoside Antibiotics. IV 3',4'-Dideoxyparomomycin and Analogues," *The Journal of Antibiotics* 35(1):98-101, Jan. 1982.

(Continued)

*Primary Examiner* — Elli Peselev

(57) ABSTRACT

The present invention is directed to analogs of aminoglycoside compounds as well as their preparation and use as prophylactic or therapeutics against microbial infection.

14 Claims, No Drawings

FOREIGN PATENT DOCUMENTS

| | | |
|---|---|---|
| WO | WO 02/053188 A1 | 7/2002 |
| WO | WO 03/059246 A2 | 7/2003 |
| WO | WO 03/101405 A2 | 12/2003 |
| WO | WO 03/105774 A2 | 12/2003 |
| WO | WO 2005/041984 A1 | 5/2005 |
| WO | WO 2006/052930 A1 | 5/2006 |
| WO | WO 2007/028012 A2 | 3/2007 |
| WO | WO 2007/064954 A2 | 6/2007 |
| WO | WO 2007/088999 A1 | 8/2007 |
| WO | WO 2008/006583 A1 | 1/2008 |
| WO | WO 2008/092690 A1 | 8/2008 |
| WO | WO 2008/124821 A1 | 10/2008 |
| WO | WO 2009/067692 A1 | 5/2009 |
| WO | WO 2010/030690 A1 | 3/2010 |
| WO | WO 2010/030704 A2 | 3/2010 |
| WO | WO 2010/042850 A1 | 4/2010 |
| WO | WO 2010/042851 A1 | 4/2010 |
| WO | WO 2010/132757 A2 | 11/2010 |
| WO | WO 2010/132759 A1 | 11/2010 |
| WO | WO 2010/132760 A1 | 11/2010 |
| WO | WO 2010/132765 A2 | 11/2010 |
| WO | WO 2010/132768 A1 | 11/2010 |
| WO | WO 2010/132770 A1 | 11/2010 |
| WO | WO 2010/132777 A2 | 11/2010 |
| WO | WO 2010/132839 A2 | 11/2010 |
| WO | WO 2010/147836 A1 | 12/2010 |
| WO | WO 2011/044498 A1 | 4/2011 |
| WO | WO 2011/044501 A2 | 4/2011 |
| WO | WO 2011/044502 A1 | 4/2011 |
| WO | WO 2011/044503 A1 | 4/2011 |
| WO | WO 2011/044538 A1 | 4/2011 |
| WO | WO 2012/067978 A1 | 5/2012 |

OTHER PUBLICATIONS

The Merck Index, twelfth edition. Budavari (ed.), Whitehouse Station: Merck & Co., Inc., Compound 1559, 1996.

Cavender et al., "Trifluoromethanesulfonyl Azide. Its Reaction with Alkyl Amines to Form Alkyl Azides," *J. Org. Chem.* 37(22):3567-3569, 1972.

Chen et al., "Structure-toxicity relationship of aminoglycosides: Correlation of 2'-amine basicity with acute toxicity in pseudo-disaccharide scaffolds," *Bioorganic & Medicinal Chemistry* 16:8940-8951, 2008.

Chow et al., "A Structural Basis for RNA—Ligand Interactions," *Chem. Rev.* 97(5):1489-1513, Jul./Aug. 1997.

Ding et al., "Efficient synthesis of neomycin B related aminoglycosides," *Tetrahedron Letters* 41:4049-4052, 2000.

Dozzo et al., "New aminoglycoside antibiotics," *Expert Opin. Ther. Patents* 20(10):1-21, 2010.

François et al., "Antibacterial Aminoglycosides with a Modified Mode of Binding to the Ribosomal-RNA Decoding Site," *Angew. Chem. Int. Ed.* 43:6735-6738, 2004.

Georgiadas et al., "Synthesis of Amino Acid Derivatives of Neamine and 2-Deoxystreptamine to Be Used as Mutasynthons," *J. Carbohydrate Chemistry* 10(5):739-748, 1991.

Greenberg et al., "Design and Synthesis of New Aminoglycoside Antibiotics Containing Neamine as an Optimal Core Structure: Correlation of Antibiotic Activity with in Vitro Inhibition of Translation," *J. Am. Chem. Soc.* 121(28):6527-6541, 1999.

Greene, "Protective Groups in Organic Synthesis," John Wiley & Sons, Inc., New York, p. 29-39, 1981.

Hanessian et al., "Aminoglycoside antibiotics: Chemical conversion of neomycin B, paromomycin, and lividomycin B into bioactive pseudosaccharides," *Canadian Journal of Chemistry* 56(11):1482-1491, Jun. 1, 1978.

Hanessian et al., "Aminoglycoside Antibiotics 4'-Deoxyneomycin and 4'-Deoxyparomamine," *The Journal of Antibiotics* 33(6):675-678, Jun. 1980.

Hanessian et al., "Probing the functional requirements of the L-haba side-chain of amikacin—synthesis, 16S A-site or rRNA binding, and antibacterial activity," *Tetrahedron* 59: 995-1007, 2003.

Hanessian et al., "Probing the ribosomal RNA A-site with functionally diverse analogues of paromomycin—synthesis of ring I mimetics," *Tetrahedron* 63:827-846, 2007.

Hermansky, "Neomycin N-methanesulfonate," Database CAPLUS on STN, Accession No. 60:11121, 1962, 2 pages.

Hoshi et al., "Amikacin Analogs with a Fluorinated Amino Acid Side Chain," *The Journal of Antibiotics* 43(7):858-872, Jul. 1990.

Kane et al., "Basicity of the Amino Groups of the Aminoglycoside Amikacin Using Capillary Electrophoresis and Coupled CE-MS-MS Techniques," *Analytical Chemistry* 73(16):4028-4036, Aug. 15, 2001.

Kondo et al., "Crystal Structure of the Bacterial Ribosomal Decoding Site Complexed with a Synthetic Doubly Functionalized Paromomycin Derivative: a New Specific Binding Mode to an A-Minor Motif Enhances in vitro Antibacterial Activity," *ChemMedChem* 2:1631-1638, 2007.

Kumar et al., "Aminoglycoside Antibiotics. 4. Regiospecific Partial Synthesis of Ribostamycin and 4"-Thioribostamycin," *J. Org. Chem.* 46(21):4298-4300, 1981.

Lesniak et al., "An isocratic separation of underivatized gentamicin components, H NMR assignment and protonation pattern," *Carbohydrate Research* 338:2853-2862, 2003.

Li et al., "Investigation of the Regioselectivity for the Staudinger Reaction and Its Application for the Synthesis of Aminoglycosides with N-1 Modification," *J. Org. Chem.* 72(11):4055-4066, 2007.

Li et al., "Guanidine/Pd(OAc)$_2$-Catalyzed Room Temperature Suzuki Cross-Coupling Reaction in Aqueous Media under Aerobic Conditions," *J. Org. Chem.* 72(11):4067-4072, 2007.

Llewellyn et al., "Chemoenzymatic acylation of aminoglycoside antibiotics," *Chem. Commun.* 32:3786-3788, 2008.

Marrero-Ponce et al., "Non-stochastic and stochastic linear indices of the molecular pseudograph's atom-adjacency matrix: a novel approach for computational in silico screening and "rational" selection of new lead antibacterial agents," *J. Mol. Model.* 12: 255-271, 2006.

Marrero-Ponce et al., "Atom, atom-type, and total nonstochastic and stochastic quadratic fingerprints: a promising approach for modeling of antibacterial activity," *Bioorganic & Medicinal Chemistry* 13:2881-2899, 2005.

Moazed et al., "Interaction of antibiotics with functional sites in 16S ribosomal RNA," *Nature* 327:389-394, Jun. 4, 1987.

Narita et al., "Synthesis and Activity of Butirosin Derivatives with 5"-Amidino and 5"Guanidino Substituents," *The Journal of Antibiotics* 44(1):86-92, Jan. 1991.

O'Shea et al., "Physicochemical Properties of Antibacterial Compounds: Implications for Drug Discovery," *Journal of Medicinal Chemistry* 51(10):2871-2878, May 22, 2008.

Pénasse et al., "Sur quelques dérivés mono N-alcoyles de la néeomycine et de la paromomycine," *Bulletin de la Société chimique de France* 7:2391-2394, Jul. 1969.

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," *Organic Letters* 1(6):953-956, 1999.

Shier et al., "Chemistry and Biochemistry of the Neomycins. XVI Synthesis and Bioactivity of Hexa-N-Benzylneomycins," *The Journal of Antibiotics* 26(10):547-550, Oct. 1973.

Sunada et al., "Enzymatic 1-N-Acetylation of Paromomycin by an Actinomycete Strain #8 with Multiple Aminoglycoside Resistance and Paromomycin Sensitivity," *The Journal of Antibiotics* 52(9):809-814, Sep. 1999.

Takahashi et al., "Syntheses of 1-Epikanamycin a and Its 1-N-[(S)-4-Amino-2- hydroxybutyryl] Derivative," *Bull. Chem. Soc. Jpn.* 56(6):1807-1811, Jun. 1983.

Takahashi et al., "Study on fluorination-toxicity relationships. Syntheses of 1-N-[(2R,3R)- and (2R,3S)-4-amino-3-fluoro-2-hydroxybutanoyl] derivatives of kanamycins," *Carbohydrate Research* 249:57-76, 1993.

Takahashi et al., "Synthesis of 1-N-[(2S,4S)- and (2S,4R)-5-amino-4-fluoro-2-hydroxypentanoyl]dibekacins (study on structure—toxicity relationships)," *Carbohydrate Research* 306:349-360, 1998.

Takamoto et al., "Aminoglycoside Antibiotics: Chemical Transformation of Paromomycin Into a Bioactive Pseudotrisaccharide," *Tetrahedron Letters* 46:4009-4012, 1974.

Takeda et al., "Mutational Biosynthesis of Butirosin Analogs II. 3',4'-Dideoxy-6'-NMethylbutirosins, New Semisynthetic Aminoglycosides," *The Journal of Antibiotics* 31(10):1031-1038, Oct. 1978.

Takeda et al., "Mutational Biosynthesis of Butirosin Analogs III. 6'-N-Methylbutirosins and 3',4'-Dideoxy-6'-C-Methylbutirosins, New Semisynthetic Aminoglycosides," *The Journal of Antibiotics* 31(10):1039-1045, Oct. 1978.

Tamura et al., "The Synthesis of Destomycin C, a Typical Pseudo-Trisaccharide of Destomycin-Group Antibiotics," *Carbohydrate Research* 174:181-199, 1988.

Taniyama et al., "Antibiotics Aminosidin. II. Some Amino Derivatives of Aminosidin and Their Biological Activity," *Chem. Pharm. Bull.* 21(3):609-615, Mar. 1973.

Tok et al., "Binding of Aminoglycoside Antibiotics with Modified A-site 16S rRNA Construct Containing Non-Nucleotide Linkers," *Bioorganic & Medicinal Chemistry Letters* 12:365-370, 2002.

Umezawa et al., "Synthesis and Antibacterial Activity of 6'-N-Alkyl Derivatives of 1-N-[(S)-4-Amino-2-Hydroxybutyryl]-Kanamycin," *The Journal of Antibiotics* 28(6):483-485, Jun. 1975.

Van Straten et al., "An Expeditious Route to the Synthesis of Adenophostin A," *Tetrahedron* 53(18):6509-6522, 1997.

Wallis et al., "The Binding of Antibiotics to RNA," *Prog. Biophys. molec. Biol.* 67(2/3):141-154, 1997.

Watanabe et al., "Syntheses of 6'-Amino-6'-Deoxylividomycin B and 6'-Deoxy-6'Methylamino- and 6'-Deoxy-6'-(2-Hydroxyethylamino)-Lividomycin B," *The Journal of Antibiotics* 26(12):802-804, Dec. 1973.

Watanabe et al., "Synthesis of 6'-Amino-1-N-[(S)-4-Amino-2-Hydroxybutyryl]-6'-Deoxylividomycin A," *Bulletin of the Chemical Society of Japan* 48(8):2303-2305, Aug. 1975.

Watanabe et al., "Synthesis of 1-$N$-[($S$)-4-Amino-2-hydroxybutyryl-]lividomycin A," *Bulletin of the Chemical Society of Japan* 48(7):2124-2126, Jul. 1975.

Watanabe et al., "Synthesis of 1-$N$-(($S$)-4-Amino-2-Hydroxybutyryl) Lividomycin A," *The Journal of Antibiotics* 26(5):310-312, May 1973.

Yamasaki et al., "Synthesis and Biological Activity of 1-$N$-[4-(Substituted)Amidino and Guanidino-2-Hydroxybutyryl]Kanamycins A and B," *The Journal of Antibiotics* 44(6):646658, Jun. 1991.

Zaloom et al., "Preparation of Azido Derivatives from Amino Acids and Peptides by Diazo Transfer," *J. Org. Chem* 46(25):5173-5176, 1981.

International Search Report for PCT International Application No. PCT/US2005/040364, mailed Mar. 29, 2006, 4 pages.

International Search Report for PCT International Application No. PCT/US2006/034216, mailed May 3, 2007, 5 pages.

International Search Report for PCT International Application No. PCT/US2006/046122, mailed Jun. 21, 2007, 7 pages.

International Search Report for PCT International Application No. PCT/US2008/059904, mailed Jun. 19, 2008, 3 pages.

International Search Report for PCT International Application No. PCT/US2009/056391, mailed Feb. 15, 2010, 5 pages.

International Search Report for PCT International Application No. PCT/US2009/056407, mailed Mar. 30, 2010, 3 pages.

International Search Report for PCT International Application No. PCT/US2009/060211, mailed Dec. 29, 2009, 3 pages.

International Search Report for PCT International Application No. PCT/US2009/060212, mailed Dec. 9, 2009, 3 pages.

International Search Report for PCT International Application No. PCT/US2010/052045, mailed Feb. 17, 2011, 4 pages.

International Search Report for PCT International Application No. PCT/US2010/052109, mailed Feb. 23, 2011, 4 pages.

International Search Report for PCT International Application No. PCT/US2010/052040, mailed Feb. 23, 2011, 3 pages.

International Search Report for PCT International Application No. PCT/US2010/052044, mailed Feb. 23, 2011, 4 pages.

International Search Report for PCT International Application No. PCT/US2010/052043, mailed May 2, 2011, 6 pages.

Invitation to Pay Additional Fees for PCT International Application No. PCT/US2010/052043, mailed Feb. 24, 2011, 8 pages.

International Preliminary Report on Patentability for PCT/US2005/040364, mailed May 8, 2007, 9 pages.

International Preliminary Report on Patentability for PCT/US2006/034216, mailed Mar. 4, 2008, 8 pages.

International Preliminary Report on Patentability for PCT/US2009/056391, mailed Mar. 15, 2011, 9 pages.

International Preliminary Report on Patentability for PCT/US2006/046122, mailed Jun. 4, 2008, 11 pages.

International Preliminary Report on Patentability for PCT/US2008/059904, mailed Oct. 13, 2009, 7 pages.

International Preliminary Report on Patentability for PCT/US2009/056407, mailed Mar. 15, 2011, 5 pages.

International Preliminary Report on Patentability for PCT/US2009/060212, mailed Apr. 12, 2011, 6 pages.

International Preliminary Report on Patentability for PCT/US2009/060211, mailed Apr. 12, 2011, 7 pages.

Written Opinion for PCT/US2005/040364, mailed Mar. 29, 2006, 8 pages.

Written Opinion for PCT/US2006/034216, mailed May 3, 2007, 7 pages.

Written Opinion for PCT/US2006/046122, mailed Jun. 21, 2007, 10 pages.

Written Opinion for PCT/US2008/059904, mailed Jun. 19, 2008, 6 pages.

Written Opinion for PCT/US2009/056391, mailed Feb. 15, 2010, 8 pages.

Written Opinion for PCT/US2009/056407, mailed Mar. 30, 2010, 5 pages.

Written Opinion for PCT/US2009/060211, mailed Dec. 29, 2009, 6 pages.

Written Opinion for PCT/US2009/060212, mailed Dec. 9, 2009, 5 pages.

Written Opinion for PCT/US2010/052045, mailed Feb. 17, 2011, 5 pages.

Written Opinion for PCT/US2010/052109, mailed Feb. 23, 2011, 6 pages.

Written Opinion for PCT/US2010/052040, mailed Feb. 23, 2011, 5 pages.

Written Opinion for PCT/US2010/052043, mailed May 2, 2011, 11 pages.

Written Opinion for PCT/US2010/052044, mailed Feb. 23, 2011, 8 pages.

Torn et al., Synthesis of 5"-Deoxy-5"-fluorolividomycin B, Bull. Chem. Soc. Jpn. 56, 56(5):1522-1526 1983.

International Search Report for PCT International Application No. PCT/US2011/060513, mailed Mar. 27, 2011, 4 pages.

International Preliminary Report on Patentability for PCT/US2010/052040, mailed Apr. 19, 2012, 7 pages.

International Preliminary Report on Patentability for PCT/US2010/052043, mailed Apr. 19, 2012, 12 pages.

International Preliminary Report on Patentability for PCT/US2010/052045, mailed Apr. 19, 2012, 7 pages.

International Preliminary Report on Patentability for PCT/US2010/052044, mailed Apr. 19, 2012, 8 pages.

Written Opinion for PCT/US2011/060513, mailed Mar. 27, 2011, 7 pages.

Non-Final Office Action for U.S. Appl. No. 12/040,615, mailed Jan. 27, 2009, 6 pages.

Non-Final Office Action for U.S. Appl. No. 12/040,615, mailed Jun. 25, 2009, 16 pages.

Notice of Abandonment for U.S. Appl. No. 12/040,615, mailed Feb. 3, 2010, 3 pages.

Non-Final Office Action for U.S. Appl. No. 09/452,606, mailed Jul. 13, 2001, 13 pages.

Office Communication for U.S. Appl. No. 09/452,606, mailed Dec. 21, 2001, 4 pages.

Final Office Action for U.S. Appl. No. 09/452,606, mailed May 7, 2002, 7 pages.

Office Communication for U.S. Appl. No. 09/452,606, mailed Feb. 5, 2003, 3 pages.

Advisory Action for U.S. Appl. No. 09/452,606, mailed Aug. 5, 2002, 3 pages.

Notice of Allowance and Fee(s) Due for U.S. Appl. No. 09/452,606, mailed Oct. 21, 2002, 3 pages.
Issue Notification for U.S. Appl. No. 09/452,606, mailed Mar. 12, 2003, 1 page.
Non-Final Office Action for U.S. Appl. No. 09/727,315, mailed Sep. 23, 2002, 7 pages.
Non-Final Office Action for U.S. Appl. No. 09/727,315, mailed Jan. 14, 2003, 10 pages.
Final Office Action for U.S. Appl. No. 09/727,315, mailed Apr. 28, 2003, 7 pages.
Notice of Allowance and Fee(s) Due for U.S. Appl. No. 09/727,315, mailed Aug. 25, 2003, 7 pages.
Notice of Allowance and Fee(s) Due for U.S. Appl. No. 09/727,315, mailed Jan. 28, 2004, 3 pages.
Issue Notification for U.S. Appl. No. 09/727,315, mailed Jun. 17, 2004, 1 page.
Non-Final Office Action for U.S. Appl. No. 10/299,220, mailed Nov. 3, 2003, 11 pages.
Notice of Non-Compliant Amendment (37 CFR 1.121) for U.S. Appl. No. 10/299,220, mailed Feb. 10, 2004, 2 pages.
Final Office Action for U.S. Appl. No. 10/299,220, mailed May 13, 2004, 10 pages including Appendices A-C.
Advisory Action for U.S. Appl. No. 10/299,220, mailed Aug. 6, 2004, 3 pages.
Notice of Allowance and Fee(s) Due for U.S. Appl. No. 10/299,220, mailed Oct. 13, 2004, 5 pages.
Response to Rule 312 Communication for U.S. Appl. No. 10/299,220, mailed Oct. 13, 2005, 2 pages.
Issue Notification for U.S. Appl. No. 10/299,220, mailed Nov. 2, 2005, 1 page.
Non-Final Office Action for U.S. Appl. No. 12/130,048, mailed May 27, 2010, 9 pages.
Notice of Allowance and Fee(s) Due for U.S. Appl. No. 12/130,048, mailed Dec. 14, 2010, 4 pages.
Issue Notification for U.S. Appl. No. 12/130,048, mailed Feb. 2, 2011, 1 page.
Non-Final Office Action for U.S. Appl. No. 12/100,981, mailed Nov. 27, 2009, 10 pages.
Non-Final Office Action for U.S. Appl. No. 12/100,981, mailed Feb. 26, 2010, 7 pages.
Final Office Action for U.S. Appl. No. 12/100,981, mailed Oct. 4, 2010, 8 pages.
Non-Final Office Action for U.S. Appl. No. 12/100,981, mailed Nov. 29, 2011, 7 pages.
Final Office Action for U.S. Appl. No. 12/100,981, mailed Jul. 6, 2012, 8 pages.
Non-Final Office Action for U.S. Appl. No. 13/044,234, mailed Apr. 27, 2012, 8 pages.
Notice of Allowance and Fee(s) Due for U.S. Appl. No. 13/082,141, mailed Aug. 6, 2012, 9 pages.
Notice of Allowance and Fee(s) Due for U.S. Appl. No. 13/082,143, mailed Aug. 9, 2012, 9 pages.
Notice of Allowance and Fee(s) Due for U.S. Appl. No. 13/295,219, mailed Jul. 30, 2012, 8 pages.

* cited by examiner

US 8,377,896 B2

ANTIBACTERIAL 4,6-SUBSTITUTED 6', 6" AND 1 MODIFIED AMINOGLYCOSIDE ANALOGS

CROSS-REFERENCE TO RELATED APPLICATION

This application is a continuation of International PCT Patent Application No. PCT/US2009/056391, which was filed on Sep. 9, 2009, now pending, which claims the benefit under 35 U.S.C. §119(e) of U.S. Provisional Patent Application No. 61/095,670, filed Sep. 10, 2008, which applications are incorporated herein by reference in their entireties.

FIELD OF THE INVENTION

The present invention is directed to novel aminoglycoside compounds and synthetic methods for their preparation and use as therapeutic or prophylactic agents.

BACKGROUND OF THE INVENTION

A particular interest in modern drug discovery is the development of novel low molecular weight orally-bioavailable drugs that work by binding to RNA. RNA, which serves as a messenger between DNA and proteins, was thought to be an entirely flexible molecule without significant structural complexity. Recent studies have revealed a surprising intricacy in RNA structure. RNA has a structural complexity rivaling proteins, rather than simple motifs like DNA. Genome sequencing reveals both the sequences of the proteins and the mRNAs that encode them. Since proteins are synthesized using an RNA template, such proteins can be inhibited by preventing their production in the first place by interfering with the translation of the mRNA. Since both proteins and the RNAs are potential drug targeting sites, the number of targets revealed from genome sequencing efforts is effectively doubled. These observations unlock a new world of opportunities for the pharmaceutical industry to target RNA with small molecules.

Classical drug discovery has focused on proteins as targets for intervention. Proteins can be extremely difficult to isolate and purify in the appropriate form for use in assays for drug screening. Many proteins require post-translational modifications that occur only in specific cell types under specific conditions. Proteins fold into globular domains with hydrophobic cores and hydrophilic and charged groups on the surface. Multiple subunits frequently form complexes, which may be required for a valid drug screen. Membrane proteins usually need to be embedded in a membrane to retain their proper shape. The smallest practical unit of a protein that can be used in drug screening is a globular domain. The notion of removing a single alpha helix or turn of a beta sheet and using it in a drug screen is not practical, since only the intact protein may have the appropriate 3-dimensional shape for drug binding. Preparation of Biologically Active Proteins for Screening is a Major Limitation in Classical high throughput screening. Quite often the limiting reagent in high throughput screening efforts is a biologically active form of a protein which can also be quite expensive.

For screening to discover compounds that bind RNA targets, the classic approaches used for proteins can be superceded with new approaches. All RNAs are essentially equivalent in their solubility, ease of synthesis or use in assays. The physical properties of RNAs are independent of the protein they encode. They may be readily prepared in large quantity through either chemical or enzymatic synthesis and are not extensively modified in vivo. With RNA, the smallest practical unit for drug binding is the functional subdomain. A functional subdomain in RNA is a fragment that, when removed from the larger RNA and studied in isolation, retains its biologically relevant shape and protein or RNA-binding properties. The size and composition of RNA functional subdomains make them accessible by enzymatic or chemical synthesis. The structural biology community has developed significant experience in identification of functional RNA subdomains in order to facilitate structural studies by techniques such as NMR spectroscopy. For example, small analogs of the decoding region of 16S rRNA (the A-site) have been identified as containing only the essential region, and have been shown to bind antibiotics in the same fashion as the intact ribosome.

The binding sites on RNA are hydrophilic and relatively open as compared to proteins. The potential for small molecule recognition based on shape is enhanced by the deformability of RNA. The binding of molecules to specific RNA targets can be determined by global conformation and the distribution of charged, aromatic, and hydrogen bonding groups off of a relatively rigid scaffold. Properly placed positive charges are believed to be important, since long-range electrostatic interactions can be used to steer molecules into a binding pocket with the proper orientation. In structures where nucleobases are exposed, stacking interactions with aromatic functional groups may contribute to the binding interaction. The major groove of RNA provides many sites for specific hydrogen bonding with a ligand. These include the aromatic N7 nitrogen atoms of adenosine and guanosine, the O4 and O6 oxygen atoms of uridine and guanosine, and the amines of adenosine and cytidine. The rich structural and sequence diversity of RNA suggests to us that ligands can be created with high affinity and specificity for their target.

Although our understanding of RNA structure and folding, as well as the modes in which RNA is recognized by other ligands, is far from being comprehensive, significant progress has been made in the last decade (Chow, C. S.; Bogdan, F. M., *Chem. Rev.*, 1997, 97, 1489, Wallis, M. G.; Schroeder, R., *Prog. Biophys. Molec. Biol.* 1997, 67, 141). Despite the central role RNA plays in the replication of bacteria, drugs that target these pivotal RNA sites of these pathogens are scarce. The increasing problem of bacterial resistance to antibiotics makes the search for novel RNA binders of crucial importance.

Certain small molecules can bind and block essential functions of RNA. Examples of such molecules include the aminoglycoside antibiotics and drugs such as erythromycin which binds to bacterial rRNA and releases peptidyl-tRNA and mRNA. Aminoglycoside antibiotics have long been known to bind RNA. They exert their antibacterial effects by binding to specific target sites in the bacterial ribosome. For the structurally related antibiotics neamine, ribostamycin, neomycin B, and paromomycin, the binding site has been localized to the A-site of the prokaryotic 16S ribosomal decoding region RNA (Moazed, D.; Noller, H. F., *Nature,* 1987, 327, 389). Binding of aminoglycosides to this RNA target interferes with the fidelity of mRNA translation and results in miscoding and truncation, leading ultimately to bacterial cell death (Alper, P. B.; Hendrix, M.; Sears, P.; Wong, C., *J. Am. Chem. Soc.,* 1998, 120, 1965).

There is a need in the art for new chemical entities that work against bacteria with broad-spectrum activity. Perhaps the biggest challenge in discovering RNA-binding antibacterial drugs is identifying vital structures common to bacteria that can be disabled by small molecule drug binding. A challenge in targeting RNA with small molecules is to develop a chemical strategy which recognizes specific shapes of RNA. There are three sets of data that provide hints on how to do this: natural protein interactions with RNA, natural product antibiotics that bind RNA, and man-made RNAs (aptamers) that bind proteins and other molecules. Each data set, however, provides different insights to the problem.

Several classes of drugs obtained from natural sources have been shown to work by binding to RNA or RNA/protein complexes. These include three different structural classes of antibiotics: thiostreptone, the aminoglycoside family and the macrolide family of antibiotics. These examples provide powerful clues to how small molecules and targets might be selected. Nature has selected RNA targets in the ribosome, one of the most ancient and conserved targets in bacteria. Since antibacterial drugs are desired to be potent and have broad-spectrum activity these ancient processes fundamental to all bacterial life represent attractive targets. The closer we get to ancient conserved functions the more likely we are to find broadly conserved RNA shapes. It is important to also consider the shape of the equivalent structure in humans, since bacteria were unlikely to have considered the therapeutic index of their RNAs while evolving them.

A large number of natural antibiotics exist, these include the aminoglycosides, kirromycin, neomycin, paromomycin, thiostrepton, and many others. They are very potent, bactericidal compounds that bind RNA of the small ribosomal subunit. The bactericidal action is mediated by binding to the bacterial RNA in a fashion that leads to misreading of the genetic code. Misreading of the code during translation of integral membrane proteins is thought to produce abnormal proteins that compromise the barrier properties of the bacterial membrane.

Antibiotics are chemical substances produced by various species of microorganisms (bacteria, fungi, actinomycetes) that suppress the growth of other microorganisms and may eventually destroy them. However, common usage often extends the term antibiotics to include synthetic antibacterial agents, such as the sulfonamides, and quinolines, that are not products of microbes. The number of antibiotics that have been identified now extends into the hundreds, and many of these have been developed to the stage where they are of value in the therapy of infectious diseases. Antibiotics differ markedly in physical, chemical, and pharmacological properties, antibacterial spectra, and mechanisms of action. In recent years, knowledge of molecular mechanisms of bacterial, fungal, and viral replication has greatly facilitated rational development of compounds that can interfere with the life cycles of these microorganisms.

At least 30% of all hospitalized patients now receive one or more courses of therapy with antibiotics, and millions of potentially fatal infections have been cured. At the same time, these pharmaceutical agents have become among the most misused of those available to the practicing physician. One result of widespread use of antimicrobial agents has been the emergence of antibiotic-resistant pathogens, which in turn has created an ever-increasing need for new drugs. Many of these agents have also contributed significantly to the rising costs of medical care.

When the antimicrobial activity of a new agent is first tested a pattern of sensitivity and resistance is usually defined. Unfortunately, this spectrum of activity can subsequently change to a remarkable degree, because microorganisms have evolved the array of ingenious alterations discussed above that allow them to survive in the presence of antibiotics. The mechanism of drug resistance varies from microorganism to microorganism and from drug to drug.

The development of resistance to antibiotics usually involves a stable genetic change, heritable from generation to generation. Any of the mechanisms that result in alteration of bacterial genetic composition can operate. While mutation is frequently the cause, resistance to antimicrobial agents may be acquired through transfer of genetic material from one bacterium to another by transduction, transformation or conjugation.

One group has prepared and assayed 6'-N-methyl and 6'-N-ethyl derivatives of amikacin (Umezawa, et al., *Journal of Antiboiotics*, 1975, 28(6), 483-485). They showed that these derivatives were hardly affected by the 6'-N-acetyltransferase which has been shown to inactivate amikacin.

For the foregoing reasons, there is a need for new chemical entities that possess antimicrobial activity. Further, in order to accelerate the drug discovery process, new methods for synthesizing aminoglycoside antibiotics are needed to provide an array of compounds that are potentially new drugs for the treatment microbial infections.

BRIEF SUMMARY OF THE INVENTION

In one aspect, the present invention provides compounds having formula I:

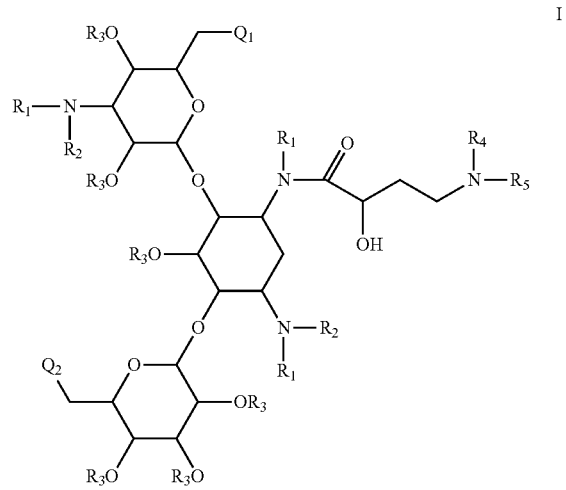

wherein:
each $R_1$ and $R_2$ is, independently, H or an amino protecting group;
each $R_3$ is, independently, H or a hydroxyl protecting group;
each $R_4$ and $R_5$ is independently, H, amino protecting group, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl or substituted $C_2$-$C_{12}$ alkynyl;
$Q_1$ is hydroxyl, a protected hydroxyl, cyano, azido, or $NR_8R_9$;
$Q_2$ is $NH_2$ or $N(CH_2R_6)R_7$;
$R_6$ and $R_7$ are each, independently, H, $C_1$-$C_{12}$ alkyl, substituted $C_1$-$C_{12}$ alkyl, $C_7$-$C_9$ alicyclic radical, substituted $C_7$-$C_9$ alicyclic radical, $C_2$-$C_{12}$ alkenyl, substituted $C_2$-$C_{12}$ alkenyl, $C_2$-$C_{12}$ alkynyl or substituted $C_2$-$C_{12}$ alkynyl;
$R_8$ and $R_9$ are each, independently, H, CN, $C_1$-$C_{12}$ alkyl, substituted $C_1$-$C_{12}$ alkyl, $C_7$-$C_9$ alicyclic radical, substituted $C_7$-$C_9$ alicyclic radical, $C_2$-$C_{12}$ alkenyl, substituted $C_2$-$C_{12}$ alkenyl, $C_2$-$C_{12}$ alkynyl or substituted $C_2$-$C_{12}$ alkynyl;
wherein said substituted groups are mono or poly substituted with optionally protected substituent groups selected from halogen, trifluoromethyl, cyano, $OJ_3$, $NJ_1J_2$, $C(=O)$—$NJ_1J_2$, $N(H)C(=O)$-$J_1$, $N(J_1)$-$(CH_2)_n$—$OJ_3$, $N(J_1)$-$(CH_2)_n$—$NJ_1J_2$, $C_5$-$C_{20}$ aryl, substituted $C_5$-$C_{20}$ aryl, $C_7$-$C_9$ alicyclic radical, substituted $C_7$-$C_9$ alicyclic radical, heterocycle radical, substituted heterocycle radical, heteroaryl, substituted heteroaryl, azido, carboxy, acyl (C(=O)—X), =O, cyano, sulfonyl (S(=O)$_2$—X) and sulfoxyl (S(=O)—X);

each X is, independently, H, $C_1$-$C_{12}$ alkyl or substituted $C_1$-$C_{12}$ alkyl;

each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—X), a heterocycle radical, a substituted heterocycle radical, heteroaryl or substituted heteroaryl;

each $J_3$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ aminoalkyl, substituted $C_1$-$C_{12}$ aminoalkyl or a hydroxyl protecting group;

n is from 1 to 20; and with the proviso that when $Q_1$ is hydroxyl or protected hydroxyl, $Q_2$ is N(CH$_2$R$_6$)R$_7$ and R$_7$ is H then R$_6$ is other than H or methyl.

In one embodiment the substituent groups are independently selected from OH, NH$_2$, N(H)alkyl, amide (C(=O)—N(H)J$_2$ or N(H)C(=O)-J$_1$), N(J$_1$)-(CH$_2$)$_n$—OJ$_3$, N(J$_1$)-(CH$_2$)$_n$—NJ$_1$J$_2$, $C_7$-$C_9$ alicyclic radical, $C_5$-$C_{20}$ aryl, substituted $C_5$-$C_{20}$ aryl, a heterocycle radical, a substituted heterocycle radical, heteroaryl or substituted heteroaryl.

In one embodiment each $R_1$ and $R_2$ is H. In a further embodiment each $R_3$ is H. In another embodiment $Q_1$ is hydroxyl. In another embodiment $Q_1$ is NR$_8$R$_9$.

In one embodiment one of R$_8$ and R$_9$ is H and the other of R$_8$ and R$_9$ is $C_1$-$C_{12}$ alkyl, substituted $C_1$-$C_{12}$ alkyl, $C_7$-$C_9$ alicyclic radical or substituted $C_7$-$C_9$ alicyclic radical. In a further embodiment one of R$_8$ and R$_9$ is H and the other of R$_8$ and R$_9$ is substituted $C_1$-$C_{12}$ alkyl wherein each of the substituents is, independently, $C_5$-$C_{20}$ aryl, substituted $C_5$-$C_{20}$ aryl, $C_7$-$C_9$ alicyclic radical, substituted $C_7$-$C_9$ alicyclic radical, heterocycle radical, substituted heterocycle radical, heteroaryl or substituted heteroaryl.

In one embodiment $Q_1$ is NH$_2$. In a further embodiment $Q_1$ is NH$_2$ and R$_7$ is H or $C_1$-$C_{12}$ alkyl. In another embodiment $Q_1$ is NH$_2$ and R$_6$ is $C_1$-$C_{12}$ alkyl, substituted $C_1$-$C_{12}$ alkyl, $C_7$-$C_9$ alicyclic radical or substituted $C_7$-$C_9$ alicyclic radical. In a further embodiment $Q_1$ is NH$_2$ and R$_6$ is substituted $C_1$-$C_{12}$ alkyl wherein each of the substituents is, independently, $C_7$-$C_9$ alicyclic radical, substituted $C_7$-$C_9$ alicyclic radical, $C_5$-$C_{20}$ aryl, substituted $C_5$-$C_{20}$ aryl, heterocycle radical, substituted heterocycle radical, heteroaryl or substituted heteroaryl. In a further embodiment $Q_1$ is NH$_2$ and R$_6$ is substituted $C_1$-$C_{12}$ alkyl wherein each of said substituents is, independently, $C_5$-$C_{20}$ aryl or substituted $C_5$-$C_{20}$ aryl.

In one embodiment $R_1$, $R_4$ and $R_5$ are each H.

In one embodiment one of R$_4$ and R$_5$ is H and the other of R$_4$ and R$_5$ is $C_1$-$C_{12}$ alkyl or substituted $C_1$-$C_{12}$ alkyl. In a further embodiment one of R$_4$ and R$_5$ is H and the other of R$_4$ and R$_5$ is $C_1$-$C_{12}$ alkyl or substituted $C_1$-$C_{12}$ alkyl and each substituent group is, independently, $C_7$-$C_9$ alicyclic radical, substituted $C_7$-$C_9$ alicyclic radical, $C_5$-$C_{20}$ aryl, substituted $C_5$-$C_{20}$ aryl, heterocycle radical, substituted heterocycle radical, heteroaryl or substituted heteroaryl. In another embodiment one of R$_4$ and R$_5$ is H and the other of R$_4$ and R$_5$ is $C_1$-$C_{12}$ alkyl or substituted $C_1$-$C_{12}$ alkyl and the other of R$_4$ and R$_5$ is substituted $C_1$-$C_{12}$ alkyl wherein each substituent group is, independently, $C_5$-$C_{20}$ aryl or substituted $C_5$-$C_{20}$ aryl.

In one embodiment each of $R_1$, $R_4$ and $R_5$ are H. In a further embodiment each of $R_1$, $R_4$ and $R_5$ are H and $Q_1$ is OH. In another embodiment each of $R_1$, $R_4$ and $R_5$ are H, $Q_1$ is OH and $R_7$ is H. In a further embodiment each of $R_1$, $R_4$ and $R_5$ are H, $Q_1$ is OH, $R_7$ is H and $R_6$ is CH$_2$—C$_6$H$_5$, CH(CH$_3$)$_2$ or (CH$_2$)$_2$—C$_6$H$_5$. In another embodiment each of $R_1$, $R_4$ and $R_5$ are H, $Q_1$ is OH and $R_6$ is H and $R_7$ is CH$_3$. In a further embodiment each of $R_1$, $R_4$ and $R_5$ are H and $Q_2$ is NH$_2$. In another embodiment each of $R_1$, $R_4$ and $R_5$ are H, $Q_2$ is NH$_2$ and $R_8$ is H. In a further embodiment each of $R_1$, $R_4$ and $R_5$ are H, $Q_2$ is NH$_2$, $R_8$ is H and $R_9$ is cyclohexyl (C$_6$H$_{11}$), (CH$_2$)$_2$—C$_6$H$_5$, CH(CH$_3$)$_2$ or CH$_3$.

In one embodiment $Q_1$ is azido or cyano. In a further embodiment $Q_1$ is azido or cyano and $Q_2$ is N(CH$_2$R$_6$)R$_7$ and R$_7$ is H or $C_1$-$C_{12}$ alkyl. In another embodiment $Q_1$ is azido or cyano and $Q_2$ is amino. In a further embodiment $Q_1$ is azido or cyano and Q2 is amino and $R_1$, $R_4$ and $R_5$ are each H.

The present invention also provides compounds that have specific stereochemistry about chiral centers having the configuration:

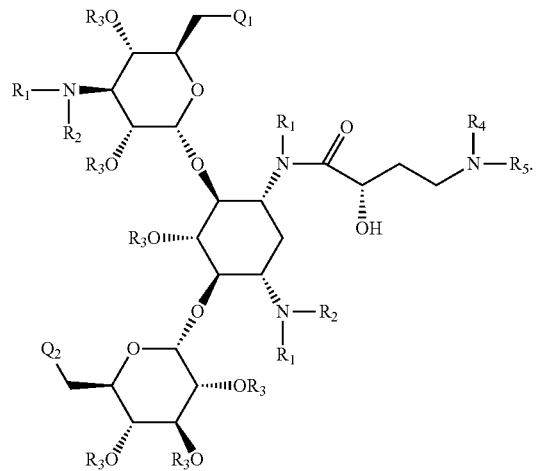

The present invention also provides methods of using a compound of the invention in therapy.

DETAILED DESCRIPTION OF THE INVENTION

The present invention provides aminoglycoside compounds having the formula I:

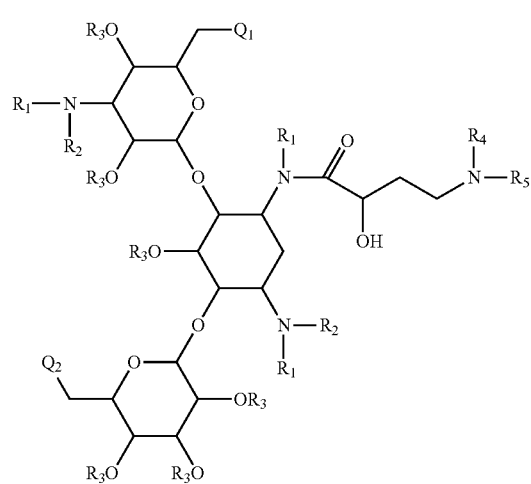

wherein:
each $R_1$ and $R_2$ is, independently, H or an amino protecting group;
each $R_3$ is, independently, H or a hydroxyl protecting group;

each $R_4$ and $R_5$ is independently, H, amino protecting group, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl or substituted $C_2$-$C_{12}$ alkynyl;

$Q_1$ is hydroxyl, a protected hydroxyl, cyano, azido, or $NR_8R_9$;

$Q_2$ is $NH_2$ or $N(CH_2R_6)R_7$;

$R_6$ and $R_7$ are each, independently, H, $C_1$-$C_{12}$ alkyl, substituted $C_1$-$C_{12}$ alkyl, $C_7$-$C_9$ alicyclic radical, substituted $C_7$-$C_9$ alicyclic radical, $C_2$-$C_{12}$ alkenyl, substituted $C_2$-$C_{12}$ alkenyl, $C_2$-$C_{12}$ alkynyl or substituted $C_2$-$C_{12}$ alkynyl;

$R_8$ and $R_9$ are each, independently, H, CN, $C_1$-$C_{12}$ alkyl, substituted $C_1$-$C_{12}$ alkyl, $C_7$-$C_9$ alicyclic radical, substituted $C_7$-$C_9$ alicyclic radical, $C_2$-$C_{12}$ alkenyl, substituted $C_2$-$C_{12}$ alkenyl, $C_2$-$C_{12}$ alkynyl or substituted $C_2$-$C_{12}$ alkynyl;

wherein said substituted groups are mono or poly substituted with optionally protected substituent groups selected from halogen, trifluoromethyl, cyano, $OJ_3$, $NJ_1J_2$, $C(=O)-NJ_1J_2$, $N(H)C(=O)$-$J_1$, $N(J_1)$-$(CH_2)_n$-$OJ_3$, $N(J_1)$-$(CH_2)_n$-$NJ_1J_2$, $C_5$-$C_{20}$ aryl, substituted $C_5$-$C_{20}$ aryl, $C_7$-$C_9$ alicyclic radical, substituted $C_7$-$C_9$ alicyclic radical, heterocycle radical, substituted heterocycle radical, heteroaryl, substituted heteroaryl, azido, carboxy, acyl (C(=O)—X), =O, cyano, sulfonyl (S(=O)$_2$—X) and sulfoxyl (S(=O)—X);

each X is, independently, H, $C_1$-$C_{12}$ alkyl or substituted $C_1$-$C_{12}$ alkyl;

each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—X), a heterocycle radical, a substituted heterocycle radical, heteroaryl or substituted heteroaryl;

each $J_3$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ aminoalkyl, substituted $C_1$-$C_{12}$ aminoalkyl or a hydroxyl protecting group;

n is from 1 to 20; and with the proviso that when $Q_1$ is hydroxyl or protected hydroxyl, $Q_2$ is $N(CH_2R_6)R_7$ and $R_7$ is H then $R_6$ is other than H or methyl.

In a preferred embodiment the compounds of the present invention are prepared from Amikacin free base which is orthogonally protected and reacted with reactive groups to place functional groups on either 6' or 6"-position. Amikacin is available from a number of commercial sources as the HCl salt and is subsequently converted to the free base. The methods are amenable to a wide variety of chemical reactions to prepare a large number of Amikacin analogs. In some preferred embodiments of the present invention each $R_1$, $R_2$, $R_3$, $R_4$ and $R_5$ is H and one of $Q_1$ and $Q_2$ is substituted with a variety of functional groups while $Q_1$ is hydroxyl or $Q_2$ is amino.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substitutent groups (see substituent group list below).

The term "alkenyl," as used herein, refers to a straight or branched hydrocarbon chain radical containing up to twenty four carbon atoms having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl or amino portions of the aminoalkyl group can be further substituted with substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines, for example. Aliphatic groups as used herein may optionally include further substitutent groups.

The term "alicyclic" refers to a cyclic ring system wherein the ring is aliphatic. The ring system can comprise one or more rings and wherein at least one ring is aliphatic. Alicyclics include rings having any degree of saturation. Preferred alicyclics include rings having from about 5 to about 9 carbon atoms in the ring. Alicyclic as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The terms "halo" and "halogen," as used herein, refer to an atom selected from fluorine, chlorine, bromine and iodine.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

The term "heterocyclic," or "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups.

The terms "heteroaryl," and "heteroaromatic," as used herein, refer to a radical comprising a mono- or poly-cyclic aromatic ring, ring system or fused ring system wherein at least one of the rings is aromatic and includes a heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined, attached to a parent molecule via an alkyl group. Examples include, but are not limited to, pyridinylmethyl, pyrimidinylethyl and the like. Heteroarylalkyl groups as used herein may optionally include further substituent groups.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The terms "substituent and substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to the parent compound. Such groups include without limitation, halogen, hydroxyl, alkyl, alkenyl, alkynyl, acyl (—C(O)$R_a$), carboxyl (—C(O)O—$R_a$), aliphatic, alicyclic, alkoxy, substituted oxo (—O—$R_a$), aryl, aralkyl, heterocyclic, heteroaryl, heteroarylalkyl, amino (—$NR_bR_c$), imino(=$NR_b$), amido (—C(O)$NR_bR_c$ or —N($R_b$)C(O)$R_a$), azido (—$N_3$), nitro (—$NO_2$), cyano (—CN), carbamido (—OC(O)$NR_bR_c$ or —N($R_b$)C(O)O$R_a$), ureido (—N($R_b$)C(O)$NR_bR_c$), thioureido (—N($R_b$)C(S)$NR_bR_c$), guanidinyl (—N($R_b$)C(=$NR_b$)$NR_bR_c$), amidinyl (—C(=$NR_b$)$NR_bR_c$ or —N($R_b$)C($NR_b$)$R_a$), thiol (—$SR_b$), sulfinyl (—S(O)$R_b$), sulfonyl (—S(O)$_2R_b$) and sulfonamidyl (—S(O)$_2NR_bR_c$ or —N($R_b$)S(O)$_2R_b$). Wherein each $R_a$, $R_b$ and $R_c$ is a further substituent group with a preferred list including without limitation alkyl, alkenyl, alkynyl, aliphatic, alkoxy, acyl, aryl, aralkyl, heteroaryl, alicyclic, heterocyclic and heteroarylalkyl.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, *Protective Groups in Organic Synthesis*, 3rd edition, John Wiley & Sons, New York (1999).

Examples of hydroxyl protecting groups include, but are not limited to, benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl (BOC), isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl (Alloc), acetyl (Ac), formyl, chloroacetyl, trifluoroacetyl, methoxyacetyl, phenoxyacetyl, benzoyl (Bz), methyl, t-butyl, 2,2,2-trichloroethyl, 2-trimethylsilyl ethyl, 1,1-dimethyl-2-propenyl, 3-methyl-3-butenyl, allyl, benzyl (Bn), para-methoxybenzyldiphenylmethyl, triphenylmethyl (trityl), 4,4'-dimethoxytriphenylmethyl (DMT), substituted or unsubstituted 9-(9-phenyl)xanthenyl (pixyl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are DMT and substituted or unsubstituted pixyl.

Examples of amino protecting groups include, but are not limited to, t-butoxycarbonyl (BOC), 9-fluorenylmethoxycarbonyl (Fmoc), benzyloxycarbonyl, and the like.

Examples of thiol protecting groups include, but are not limited to, triphenylmethyl (Trt), benzyl (Bn), and the like.

Included within the scope of the present invention are the pharmaceutically acceptable salts of the foregoing compounds. As used herein, the term "pharmaceutically acceptable salts" refers to non-toxic acid addition salts and alkaline earth metal salts of the compounds of the invention. The salts can be prepared in situ during the final isolation and purification of the compounds of the invention, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts.

As per MIC assays performed using some preferred compounds of the invention it has been found that the compounds possess antibacterial activity against at least P aeruginosa 29248, P aeruginosa 27853, P aeruginosa 25416, P. vulgaris 8427, A. bauman11 WR-2, E. coli 25922 and S. aureus 13709. The compounds of the invention are therefore useful in antibiotic treatments. In addition, the compounds, by reason of their in vitro activity, may be used in scrub solutions for surface inhibition of bacterial growth e.g. in sterilization of glasswear or as an additive in fabric laundering compositions.

Susceptible organisms generally include those gram positive and gram negative, aerobic and anaerobic organisms whose growth can be inhibited by the compounds of the invention such as Staphylococcus, Lactobacillus, Streptococcus, Sarcina, Escherichia, Enterobacter, Klebsiella, Pseudomonas, Acinetobacter, Proteus, Campylobacter, Citrobacter, Nisseria, Baccillus, Bacteroides, Peptococcus, Clostridium, Salmonella, Shigella, Serratia, Haemophilus, Brucella and other organisms.

EXAMPLES

NMR: NMR spectra were recorded on a 300 M Hz Bruker.

LCMS Method A: A 4×125 mm 5 uM Polar RP column using a gradient of 5% $CH_3CN$ (aq) to 75% $CH_3CN$ (aq) buffered with 10 mM $NH_4OAc$. The eluent was run through a UV cell and then split between an ELSD detector and an Agilent MSD1100.

LCMS Method B: A 4×125 mm 5 uM Phenomenex Aqua column using a gradient of 5% $CH_3CN$ (aq) to 75% $CH_3CN$ (aq) buffered with 10 mM $NH_4OAc$. The eluent was run through a UV cell and then split between an ELSD detector and an Agilent MSD1100.

Example 1

Preparation of 1-N-[4-(tert-butoxycarbonyl)amino-2-S-hydroxybutyryl]kanamycin A

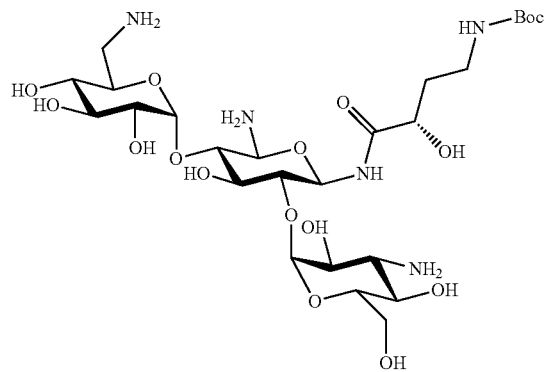

Amikacin sulfate 1.0 grams (Commercially available from a number of chemical companies: O.M. Chemical Co., Ltd., Shanghai, China; Zhejiang Winsun Imp. & Exp. Co., Ltd, Zhejiang, China; Ningbo DHY Pharmaceutical Co., Zhejiang, China; and Shanghai Xudong Haipu Pharmaceutical Co., Ltd, Shanghai, China) was treated with 4 grams of Amberlite ion exchange resin (OH— form, Aldrich, Milwaukee, Wis.) in 10 mL of water for 1 hour. The resultant solution was filtered and lyophilized to give Amikacin Free Base. The Amikacin free base (5.0 g, 8.5 mmoles) was dissolved in a mixture of 1,4-dioxane (165 mL) and $H_2O$ (235 mL). To this solution was added tert-butyloxycarbonyloxy-5-norbornene-2,3-dicarboxamide (1.3 g, 7.8 mmoles) dissolved in a mixture of $CH_2Cl_2$ (10 mL) and 1,4-dioxane (5 mL), over 50 min at room temperature. The reaction was stirred at room temp for 3 hours, and then evaporated under reduced pressure. The resultant solid was subjected to silica gel chromatography (4:4:2, MeOH, $CH_2Cl_2$, $NH_4OH$, $R_f$=0.25) and then lyophilized to give the title compound, 1.6 g (30%) as a white solid.

$^1$H NMR ($D_2O$, 300 MHz) δ 5.45 (d, 1H, J=3.3 Hz), 5.05 (d, 1H, J=3.3 Hz), 4.06 (m, 1H), 3.94 (m, 2H), 3.7 (m, 4H), 3.6-3.5 (m, 5H), 3.4-3.0 (m, 7H), 1.99 (m, 1H), 1.87 (m, 1H), 1.66 (m, 1H), 1.52 (m, 1H), 1.34 (s, 9H). $^{13}$C NMR ($D_2O$, 75 MHz) δ 175.3 (HABA, C=O), 157.2 (Boc, C=O), 97.0, 96.3, 81.2, 80.1 (Boc, quaternary), 79.5, 73.1, 71.3, 71.0, 70.2, 70.0, 68.3, 68.0, 67.7, 65.6, 58.9 ($CH_2$), 53.9, 48.2, 47.3, 39.4 ($CH_2$), 35.5 ($CH_2$), 32.44 ($CH_2$), 31.7 ($CH_2$), 26.7. LCMS Method A; (retention time, m/z) 2.14 min, 686.2 (M+H) and 708.1 (M+Na). Starting material ($R_f$=0.10) was also recovered (1.7 g, 38%). In addition, one more compound was recovered ($R_f$=0.74) and had a mass spectrum consistent with 6'-N-(tert-butoxycarbonyl)-1-N-[4-(tert-butoxycarbonyl)amino-2-S-hydroxybutyryl]-kanamycin A (1.47 g, 24%). LCMS Method A; (retention time, m/z) 2.68 min, 820.2 (M+H) and 842.2 (M+Na).

Example 2

Preparation of 6'-N-(benzyloxycarbonyl)-1-N-[4-(tert-butoxycarbonyl)amino-2-S-hydroxybutyryl]-kanamycin A

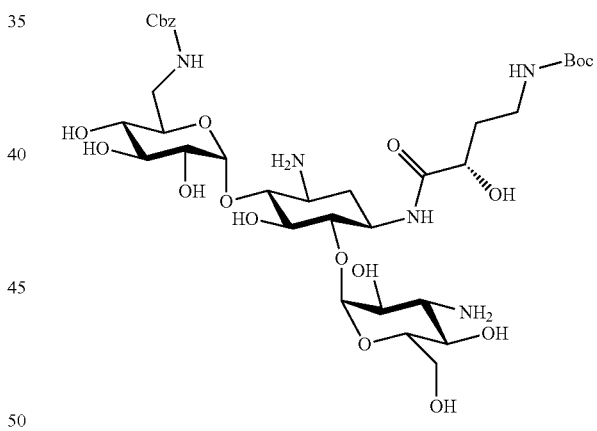

1-N-[4-(tert-butoxycarbonyl)amino-2-S-hydroxybutyryl] kanamycin A (2.4 g, 3.5 mmoles) was dissolved in a mixture of 1,4-dioxane (9 mL) and water (9 mL) at room temperature. To this solution was added benzyloxycarbonyloxy-5-norbornene-2,3-dicarboxamide (1.0 g, 3.2 mmoles), dissolved in 1,4-dioxane (2 mL), over 20 minutes at room temperature. The reaction was stirred for 1 hour, and then evaporated under reduced pressure. The resultant solid was subjected to silica gel chromatography (6:2:1.5:0.5, $CH_2Cl_2$, MeOH, 1,4-dioxane, $NH_4OH$, $R_f$=0.36) and then lyophilized to give the title compound 1.0 g (38%) as a white solid.

$^1$H NMR (DMSO-$d_6$/$D_2O$, 300 MHz) δ 7.4 (m, 5H), 5.04 (d, 1H, J=12.6 Hz), 4.96 (d, 1H, J=12.6 Hz), 4.96 (d, 1H, J=3.3 Hz), 4.88 (d, 1H, J=3.3 Hz), 3.83 (dd, 1H, J=9.3, 3.3 Hz), 3.8-3.6 (m, 5H), 3.6-3.35 (m, 7H), 3.35-2.8 (m, 10H), 1.85 (m, 1H), 1.88 (m, 1H), 1.53 (m, 1H), 1.33 (s, 9H), 1.17 (m, 1H). $^{13}$C NMR (DMSO-$d_6$/$D_2O$, 75 MHz) δ 173.8

(HABA, C=O), 156.2, 155.6, (137.2, 128.3 and 127.7, Ph), 101.3, 97.5, 97.5, 80.0, 77.5, 74.8, 72.8, 72.7, 72.2, 71.5, 71.4, 71.3, 69.2, 68.4, 60.2, 54.7, 49.5, 48.7, 42.0 36.8, 35.5, 34.2, 28.2. LCMS Method A; (retention time, m/z) 2.68 min, 820.3 (M+H) and 842.2 (M+Na). One additional compound was recovered ($R_f$=0.51).

Example 3

Preparation of 3,3''-N,N-di-(tert-butoxycarbonyl)-1-N-[4-(tert-butoxycarbonyl)-amino-2-S-hydroxybutyryl]kanamycin A

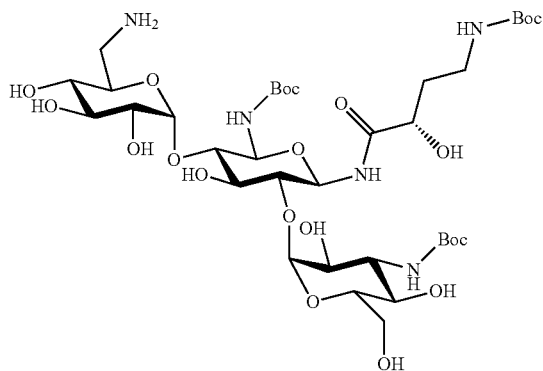

6'-N-(Benzyloxycarbonyl)-1-N-[4-(tert-butoxycarbonyl) amino-2-S-hydroxybutyryl]-kanamycin A (0.99 g, 2.9 mmoles) was dissolved in 1,4-dioxane (15 mL)/H$_2$O (5 mL) and then treated dropwise with di-tert-butyl dicarbonate (0.78 g, 3.6 mmoles) in 1,4-dioxane (3 mL) over 10 minutes at room temperature. The reaction was stirred for 16 hours and then evaporated to give a white solid. The solid was suspended in tert-butylmethylether (30 mL) and then decanted twice. The resultant solid (0.90 g, 73%) was used without further purification. TLC; (6:2:1.5:0.5, CH$_2$Cl$_2$, MeOH, 1,4-dioxane, NH$_4$OH, $R_f$=0.42). A portion of this solid (780 mg, 0.77 mmoles) was treated with 10% Pd/C (70 mg) in 90% MeOH (60 mL) under a 10 psi H$_2$ atmosphere for 3 hours to give a 93% yield of the title compound (627 mg) as the HCl salt.

Example 4

General Procedure for Reductive Amination and Deprotection

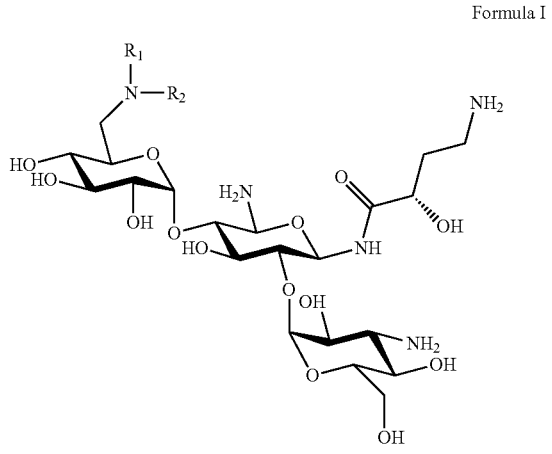

Formula I 3,3''-N,N-di-(tert-butoxycarbonyl)-1-N-[4-(tert-butoxycarbonyl)amino-2-S-hydroxybutyryl]kanamycin A (120 mg, 0.135 mmoles) is dissolved in MeOH (2 mL), trimethylorthoformate (5 mL), tetrahydrofuran (5 mL) and acetic acid (400 mL). To this stirred mixture is added 1-4 equiv of an aldehyde (R$_1$—C(=O)H) with stirring for 1 hour followed by addition of Na(CN)BH$_3$ (50 mg). The mixture is allowed to stir overnight, evaporated under reduced pressure and purified by flash chromatography (6:2:1:1.5:0.5, CH$_2$Cl$_2$, MeOH, 1,4-dioxane, NH$_4$OH). The product fractions are evaporated under reduced pressure and the residue is dried under reduced pressure overnight, and then treated with 1N HCl in dioxane (2 mL) for 1 hour. The solvent is decanted and the solid is washed with CH$_3$CN (4 mL×3) and subsequently dried under reduced pressure to give the 6'-substituted fully deprotected aminoglycoside as its HCl salt. In most of the syntheses the R$_1$ group derives from the selected aldehyde R$_1$—C(=O)H and R$_2$ is H. In some cases it is possible to get disubstitution where R$_1$ and R$_2$=R$_1$ from the aldehyde but aside from the formaldehyde example giving R$_1$=R$_2$=CH$_3$ almost exclusively, the percentage of disubstitution is minimal and the monosubstituted compound can be purified by column chromatography.

Example 5

Preparation of (IBIS00561961): 6'-N,N-Dimethyl-N-1-(4-amino-2-S-hydroxybutyryl)kanamycin A, Formula I, R$_1$=R$_2$=CH$_3$ Using 112 mg of 3,3''-N,N-di-(tert-butoxycarbonyl)-1-N-[4-(tert-butoxycarbonyl)amino-2-S-hydroxybutyryl]kanamycin A and formaldehyde (4 equiv) and following the general procedure for reductive amination at the 6'-position illustrated above gives 35 mg (37%) of the title compound as the HCl salt. Formaldehyde is an example of an aldehyde that predominantly give disubstitution. Most other aldehydes give mono substitution with a small percentage if any of the disubstitution product.

LCMS Method A; (retention time, m/z) 0.4 min, 614.2 (M+H).

Example 6

Preparation of (IBIS00561962): 6'-N-Phenpropylamino-N-1-(4-amino-2-S-hydroxybutyryl)kanamycin A, Formula I, R$_1$=Ph(CH$_2$)$_3$, R$_2$=H Using 120 mg of 3,3''-N,N-di-(tert-butoxycarbonyl)-1-N-[4-(tert-butoxycarbonyl)amino-2-S-hydroxybutyryl]kanamycin A and phenpropanal (1 equiv) and following the general procedure for reductive amination at the 6'-position illustrated above gives 28 mg (24%) of the title compound as the HCl salt.

LCMS Method A; (retention time, m/z) 0.4 min, 704.3 (M+H).

Example 7

Preparation of (IBIS00561960): 6'-N-Phenethylamino-N-1-(4-amino-2-S-hydroxybutyryl)kanamycin A, Formula I, R$_1$=Ph(CH$_2$)$_2$, R$_2$=H Using 152 mg of 3,3''-N,N-di-(tert-butoxycarbonyl)-1-N-[4-(tert-butoxycarbonyl)amino-2-S-hydroxybutyryl]kanamycin A and phenylacetaldehyde (1 equiv) and following the general procedure for reductive amination at the 6'-position illustrated above gives 30 mg (27%) of the title compound as the HCl salt.

LCMS Method A; (retention time, m/z) 0.4 min, 690.4 (M+H).

Example 8

Preparation of (IBIS00561963): 6'-N-Isobutyl-N-1-(4-amino-2-S-hydroxybutyryl)kanamycin A, Formula I, $R_1$=$(CH_3)_2CHCH_2$, $R_2$=H Using 99 mg of 3,3''-N,N-di-(tert-butoxycarbonyl)-1-N-[4-(tert-butoxycarbonyl)amino-2-S-hydroxybutyryl]kanamycin A and isobutyrylaldehyde (1 equiv) and following the general procedure for reductive amination at the 6'-position illustrated above gives 40 mg (37%) of the title compound as the HCl salt.

LCMS Method A; (retention time, m/z) 0.4 min, 642.6 (M+H).

Example 9

Preparation of 6'-deoxy-6-azido-N-1-(4-amino-2-S-hydroxybutyryl)kanamycin A,

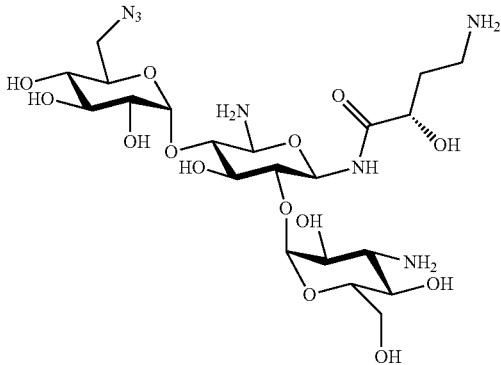

Sodium azide (1.89, 2.9 mmol) was dissolved in 5 mL of water and to this stirred solution, at room temperature, was added $CH_2Cl_2$ (6 mL) and the biphasic solution was cooled to 0° C. Triflic anhydride (1.0 mL, 6.0 mmol) in $CH_2Cl_2$ (6 mL) was added dropwise over 20 minutes and the solution was stirred for an additional 2 hours at 25° C. The organic layer was then separated and the aqueous phase extracted with $CH_2Cl_2$ (2×50 mL). The combined organic layers were washed with $NaHCO_3$ until the gas evolution ceased, and the organic phase was separated and held for the next step. 3,3''-N,N-di-(tert-butoxycarbonyl)-1-N-[4-(tert-butoxycarbonyl)amino-2-S-hydroxybutyryl]kanamycin A (2 mmoles) was treated with the above solution for 4 hours to give the title compound.

LCMS Method A; (retention time, m/z) 0.3 min, 612.2 (M+H).

Example 10

Preparation of 6'-Tosyl-6',3,3''-N-(tert-butoxycarbonyl)-1-N-[4-(tert-butoxycarbonyl)amino-2-S-hydroxybutyryl]kanamycin A

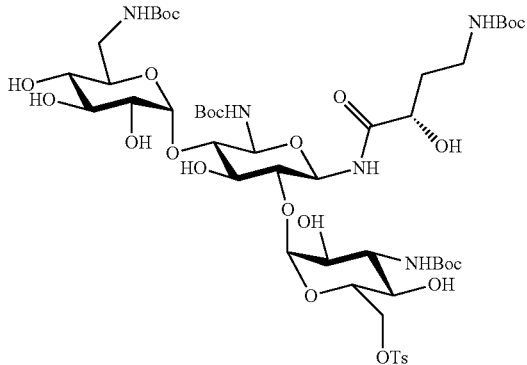

Amikacin free base (5.0 g, 8.5 mmoles) was dissolved in a mixture of 1,4-dioxane (25 mL), $Et_3N$ (5 mL) and $H_2O$ (25 mL). To this solution was added tert-butyloxycarbonylanhydride (43 mmoles) dissolved in a mixture of $CH_2Cl_2$ (5 mL) and 1,4-dioxane (5 mL), over 50 minutes at room temperature. The reaction was stirred at room temperature overnight and evaporated under reduced pressure. The resultant solid was washed several times with $Et_2O$, and then dried to give a 99% yield of tetra-N—BOC-Amikacin.

LCMS Method A; (retention time, m/z) 2.14 min, 686.2 (M+H) and 708.1 (M+Na).

Without further purification, the white solid was dissolved in dry pyridine (50 mL), cooled in an ice water bath and then treated dropwise with tosylchloride (1.8 g, 9.3 mmoles) dissolved in pyridine (5 mL). The reaction was allowed to proceed for 5 hours and then quenched with $NH_4Cl$. Water (100 mL) was added and the product was extracted with EtOAc (3×100 mL). The organic layer was subsequently washed with brine (300 mL), dried ($Na_2SO_4$), filtered and evaporated to dryness. The crude solid was purified by flash chromatography (95:5, $CH_2Cl_2$:MeOH) to give 4.8 g (50%) of the title compound as a white solid.

LCMS Method A; (retention time, m/z) 3.35 min, 1041.2 (M+H-Boc).

Example 11

General Procedure for Tosylate Displacement and Deprotection

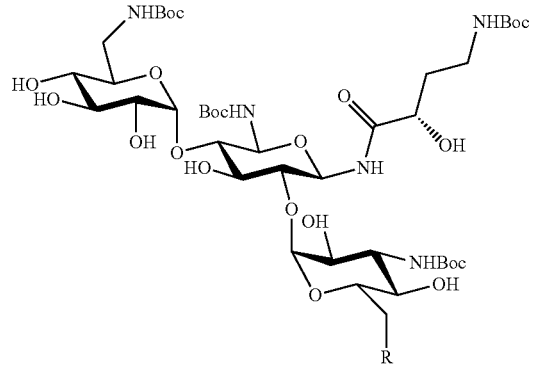

6'-Tosyl-6',3,3''-N-(tert-butoxycarbonyl)-1-N-[4-(tert-butoxycarbonyl)amino-2-S-hydroxybutyryl]-kanamycin A (100 mg, 87.7 mmoles) is treated with 10-40 equiv of a selected nucleophile and EtOH (4 mL) in a sealed tube at 70° C. After 24 to 96 hours, the reaction is cooled to room temperature, and then evaporated to dryness. The resultant crude material is purified by flash chromatography (6:2:1:1.5:0.5, $CH_2Cl_2$, MeOH, 1,4-dioxane, $NH_4OH$). The resultant solid is dried under reduced pressure overnight, and then treated with 1N HCl in dioxane (2 mL) for 1 hour. At that time, the solvent is decanted and the solid is washed with $CH_3CN$ (4 mL×3) and subsequently dried under reduced pressure to give the 6''-substituted fully deprotected aminoglycoside as its HCl salt.

Example 12

Preparation of Example 1 (IBIS00561974): 6''-deoxy-6''-methylamino-N-1-(4-amino-2-S-hydroxybutyryl)kanamycin A, R=N(H)$CH_3$ Using 100 mg of 6'-Tosyl-6',3,3''-N-(tert-butoxycarbonyl)-1-N-[4-(tert-butoxycarbonyl)amino-2-S-hydroxybutyryl]-kanamycin A and methylamine (40 equiv) and following the general procedure for tosylate displacement and deprotection illustrated above gives 57 mg (63%) of the title compound as the HCl salt.

LCMS Method A; (retention time, m/z) 0.3 min, 599.2 (M+H).

Example 13

Preparation of Example 1 (IBIS00561977): 6"-deoxy-6"-phenethylamino-N-1-(4-amino-2-S-hydroxybutyryl)kanamycin A, R=NH(CH$_2$)$_2$Ph Using 100 mg of 6'-Tosyl-6',3,3"-N-(tert-butoxycarbonyl)-1-N-[4-(tert-butoxycarbonyl)amino-2-S-hydroxybutyryl]-kanamycin A and phenethylamine (10 equiv) and following the general procedure for tosylate displacement and deprotection illustrated above gives 29 mg (29%) of the title compound as the HCl salt.

LCMS Method A; (retention time, m/z) 0.3 min, 690.2 (M+H).

Example 14

Preparation of Example 1 (IBIS00561980): 6"-deoxy-6"-azido-N-1-(4-amino-2-S-hydroxybutyryl)kanamycin A, R=N$_3$ Using 152 mg of 6'-Tosyl-6',3,3"-N-(tert-butoxycarbonyl)-1-N-[4-(tert-butoxycarbonyl)amino-2-S-hydroxybutyryl]-kanamycin A and sodium azide (10 equiv) and following the general procedure for tosylate displacement and deprotection illustrated above gives 120 mg (85%) of the title compound as the HCl salt.

LCMS Method A; (retention time, m/z) 0.3 min, 611.2 (M+H).

Example 15

Preparation of (IBIS00561976): 6"-deoxy-6"-cyclohexylamino-N-1-(4-amino-2-S-hydroxybutyryl)kanamycin A, R=cyclohexylamine Using 120 mg of 6'-Tosyl-6',3,3"-N-(tert-butoxycarbonyl)-1-N-[4-(tert-butoxycarbonyl)amino-2-S-hydroxybutyryl]-kanamycin A and cyclohexylamine (20 equiv) and following the general procedure for tosylate displacement and deprotection illustrated above gives 89 mg (75%) of the title compound as the HCl salt.

LCMS Method A; (retention time, m/z) 0.3 min, 667.2 (M+H).

Example 16

Preparation of (IBIS00561975): 6"-deoxy-6"-isopropylamino-N-1-(4-amino-2-S-hydroxybutyryl)kanamycin A, R=NHCH(CH$_3$)$_2$ Using 100 mg of 6'-Tosyl-6',3,3"-N-(tert-butoxycarbonyl)-1-N-[4-(tert-butoxycarbonyl)amino-2-S-hydroxybutyryl]-kanamycin A and isopropylamine (20 equiv) and following the general procedure for tosylate displacement and deprotection illustrated above gives 77 mg (82%) of the title compound as the HCl salt.

LCMS Method A; (retention time, m/z) 0.3 min, 627.2 (M+H).

Example 17

Preparation of (IBIS00561982): 6"-deoxy-6"-propylamino-N-1-(4-amino-2-S-hydroxybutyryl)kanamycin A, R=NH(CH$_2$)$_2$CH$_3$ Using 109 mg of 6'-Tosyl-6',3,3"-N-(tert-butoxycarbonyl)-1-N-[4-(tert-butoxycarbonyl)amino-2-S-hydroxybutyryl]-kanamycin A and propylamine (20 equiv) and following the general procedure for tosylate displacement and deprotection illustrated above gives 68 mg (72%) of the title compound as the HCl salt.

LCMS Method A; (retention time, m/z) 0.3 min, 627.2 (M+H).

Example 18

Preparation of (IBIS00561983): 6"-deoxy-6"-dimethylaminoethylamino-N-1-(4-amino-2-S-hydroxybutyryl)kanamycin A, R=NH(CH$_2$)$_2$N(CH$_3$)$_2$ Using 64 mg of 6'-Tosyl-6',3,3"-N-(tert-butoxycarbonyl)-1-N-[4-(tert-butoxycarbonyl)amino-2-S-hydroxybutyryl]-kanamycin A and N,N-dimethylamino-ethylamine (10 equiv) and following the general procedure for tosylate displacement and deprotection illustrated above gives 21 mg (21%) of the title compound as the HCl salt.

LCMS Method A; (retention time, m/z) 0.3 min, 656.3 (M+H).

Example 19

Preparation of (IBIS00561984): 6"-deoxy-6"-benzylaminoethylamino-N-1-(4-amino-2-S-hydroxybutyryl)kanamycin A, R=NH(CH$_2$)$_2$NHBn Using 99 mg of 6'-Tosyl-6',3,3"-N-(tert-butoxycarbonyl)-1-N-[4-(tert-butoxycarbonyl)amino-2-S-hydroxybutyryl]-kanamycin A and N-1-benzylamino-ethylamine (10 equiv) and following the general procedure for tosylate displacement and deprotection illustrated above gives 37 mg (34%) of the title compound as the HCl salt.

LCMS Method A; (retention time, m/z) 0.3 min, 718.3 (M+H).

Example 20

Removal of 4-amino-2-S-hydroxybutyryl side chain (IBIS00561957): 6"-deoxy-6"-phenethylamino-kanamycin A 6"-deoxy-6"-phenethylamino-N-1-(4-amino-2-S-hydroxybutyryl) kanamycin A (100 mg) was refluxed in 2N NaOH for 1-2 days to give the title compound.

LCMS Method A; (retention time, m/z) 0.3 min, 589.2 (M+H).

Example 21

Assay to Determine the Minimum Inhibitory Concentrations (MICs, Bacteria)

The MIC assays are carried out in 150 μL volume in duplicate in 96-well clear flat-bottom plates. The bacterial suspension from an overnight culture growth in appropriate medium is added to a solution of test compound in 2.5% DMSO in water. Final bacterial inoculum is approximately $10^2$-$10^3$ CFU/well. The percentage growth of the bacteria in test wells relative to that observed for control wells containing no compound is determined by measuring absorbance at 595 nm ($A_{595}$) after 20-24 hours at 37° C. The MIC is determined as a range of concentration where complete inhibition of growth is observed at the higher concentration and bacterial cells are viable at the lower concentration. Both ampicillin and tetracycline are used as antibiotic positive controls in each screening assay. Both ampicillin and tetracycline are used as antibiotic-positive controls in each screening assay for *S. pyogenes, E. coli* imp-, *E. coli, S. aureus, E. faecalis, K. pneumoniae* and *P. vulgaris*. Ciprofloxacin is used as an antibiotic positive control in each screening assay for *P. aeruginosa*.

Selected compounds were assayed for antibacterial activity with the result tabulated below:

| Compound ID | Comments | P aeruginosa 25416 | P aeruginosa 29248 | P aeruginosa 27853 |
|---|---|---|---|---|
| IBIS00404962 | Amikacin | <0.625 | 1.25-2.5 | 0.6-1.25 |
| IBIS00262400 | Kanamycin A | 2.5-5 | 1.25-2.5 | >40 |
| IBIS00561960 | | 5-10 | 2.5-5.0 | >40 |
| IBIS00561961 | | >40 | 10-20 | >40 |
| IBIS00561962 | | 2.5-5.0 | 2.5-5.0 | >40 |
| IBIS00561963 | | >40 | 10-20 | >40 |
| IBIS00561957 | | NA | NA | NA |
| IBIS00561975 | | 10-20 | 10-20 | 2.5-5.0 |
| IBIS00561976 | | 5-10 | >40 | >40 |
| IBIS00561977 | | 5-10 | 10-20 | 5-10 |
| IBIS00561974 | | 0.625-1.25 | 2.5-5.0 | 1.25-2.5 |
| IBIS00561980 | | 0.625-1.25 | 2.5-5.0 | 1.25-2.5 |
| IBIS00561982 | | 2.5-5.0 | 5.0-10.0 | 1.25-2.5 |
| IBIS00561983 | | 1.25-2.5 | 1.25-2.5 | 1.25-2.5 |
| IBIS00561984 | | 5.0-10.0 | 5.0-10.0 | 5-10 |

| Compound ID | P. vulgaris 8427 | A. bauman11 WR-2 | E. coli 25922 | S. aureus 13709 |
|---|---|---|---|---|
| IBIS00404962 | <0.625 | 0.625-1.25 | 1.25-2.5 | 5-10 |
| IBIS00262400 | >40 | 0.6-1.25 | >40 | 1.25-2.5 |
| IBIS00561960 | >40 | 2.5-5.0 | >40 | >40 |
| IBIS00561961 | 20-40 | 2.5-5.0 | 20-40 | 20-40 |
| IBIS00561962 | >40 | 1.25-2.5 | >40 | >40 |
| IBIS00561963 | >40 | 2.5-5.0 | >40 | >40 |
| IBIS00561957 | NA | NA | >10 | 5.0-10.0 |
| IBIS00561975 | 10-20 | 1.25-2.5 | 10-20 | 10-20 |
| IBIS00561976 | >40 | 5-10 | 5-10 | 5-10 |
| IBIS00561977 | 10-20 | 1.25-2.5 | 5-10 | 5-10 |
| IBIS00561974 | 1.25-2.5 | 2.5-5.0 | 10-20 | 20-40 |
| IBIS00561980 | <0.625 | 2.5-5.0 | 2.5-5 | 5-10 |
| IBIS00561982 | 2.5-5.0 | 5.0-10.0 | 5-10 | 5-10 |
| IBIS00561983 | 1.25-2.5 | 2.5-5.0 | 5-10 | 5-10 |
| IBIS00561984 | 1.25-2.5 | 10.0-20.0 | 5-10 | >40. |

Example 22

Mass Spectrometry Based Binding Assay

Screening is performed by measuring the formation of non-covalent complexes between a single ligand or ligand mixture and the appropriate RNA target, along with suitable control structured RNA target(s) simultaneously using a 9.4 T FT-ICR mass spectrometer as detector. Full experimental details of the assay have been described in related literature (Sannes-Lowery, et al. in TrAC, Trends Anal. Chem. 2000, 19, 481-491 and Sannes-Lowery, et al. in Anal. Biochem. 2000, 280, 264-271. In a typical experiment, 10 µL of an aqueous solution containing 100 mM ammonium acetate buffer, 2.5 or 5 µM of each RNA, and 33% isopropyl alcohol (to aid ion desolvation) is prepared with different concentrations of each ligand or ligand mixture Samples are introduced into the electrospray ionization source (negative ionization mode) at 1 µL/min and ions are stored for 1 sec in an RF-only hexapole following desolvation. The abundances were integrated from the respective ions for free RNA and the ligand-RNA complex. The primary (1:1 RNA:ligand) and secondary (1:2 complex, if observed) KD values are determined by titrating a single ligand through a concentration range of 0.25-25 µM with an RNA target concentration of 0.10 µM. The peak ratios are measured at each concentration, then a plot of complex/free RNA versus concentration of ligand added is fitted to a second (or higher) order binding polynomial to determine the KD.

Each reference cited herein, including but not limited to, patents, patent applications, patent publications, articles, treatises, and texts, is hereby incorporated by reference in its entirety.

What is claimed is:
1. A compound of formula I:

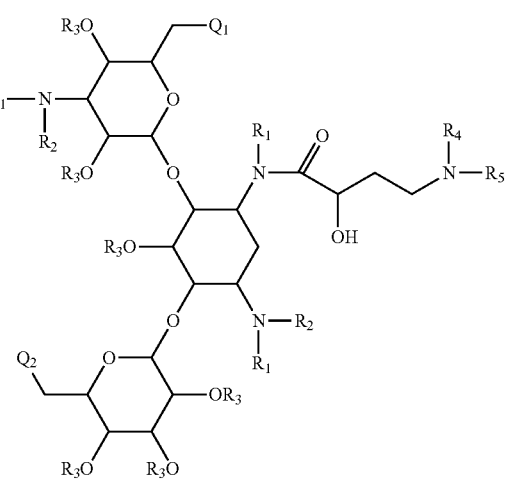

or a pharmaceutically acceptable salt thereof,
wherein:
  each $R_1$ and $R_2$ is, independently, H or an amino protecting group;
  each $R_3$ is, independently, H or a hydroxyl protecting group;
  $R_4$ and $R_5$ are each, independently, H, amino protecting group, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl or substituted $C_2$-$C_{12}$ alkynyl;
  $Q_1$ is cyano, azido, or $NR_8R_9$;
  $Q_2$ is $NH_2$ or $N(CH_2R_6)R_7$;

$R_6$ and $R_7$ are each, independently, H, $C_1$-$C_{12}$ alkyl, substituted $C_1$-$C_{12}$ alkyl, $C_7$-$C_9$ alicyclic radical, substituted $C_7$-$C_9$ alicyclic radical, $C_2$-$C_{12}$ alkenyl, substituted $C_2$-$C_{12}$ alkenyl, $C_2$-$C_{12}$ alkynyl or substituted $C_2$-$C_{12}$ alkynyl; and $R_8$ and $R_9$ are each, independently, H, CN, $C_1$-$C_{12}$ alkyl, substituted $C_1$-$C_{12}$ alkyl, $C_7$-$C_9$ alicyclic radical, substituted $C_7$-$C_9$ alicyclic radical, $C_2$-$C_{12}$ alkenyl, substituted $C_2$-$C_{12}$ alkenyl, $C_2$-$C_{12}$ alkynyl or substituted $C_2$-$C_{12}$ alkynyl;

wherein said substituents are each, independently, $NJ_1J_2$ or $C_5$-$C_{20}$ aryl; and wherein each $J_1$ and $J_2$ is, independently, H, $C_1$-$C_{12}$ alkyl or $C_5$-$C_{20}$ aryl.

2. The compound of claim 1 wherein each $R_1$ and $R_2$ is H.
3. The compound of claim 1 wherein each $R_3$ is H.
4. The compound of claim 1 wherein $Q_1$ is $NR_8R_9$.
5. The compound of claim 4 wherein one of said $R_8$ and $R_9$ is H and the other of said $R_8$ and $R_9$ is $C_1$-$C_{12}$ alkyl, substituted $C_1$-$C_{12}$ alkyl, $C_7$-$C_9$ alicyclic radical or substituted $C_7$-$C_9$ alicyclic radical.
6. The compound of claim 1 wherein $Q_1$ is $NH_2$.
7. The compound of claim 6 wherein $R_7$ is H or $C_1$-$C_{12}$ alkyl.
8. The compound of claim 6 wherein $R_6$ is $C_1$-$C_{12}$ alkyl, substituted $C_1$-$C_{12}$ alkyl, $C_7$-$C_9$ alicyclic radical or substituted $C_7$-$C_9$ alicyclic radical.
9. The compound of claim 8 wherein $R_6$ is substituted $C_1$-$C_{12}$ alkyl.
10. The compound of claim 1 wherein one of $R_4$ and $R_5$ is H and the other of $R_4$ and $R_5$ is $C_1$-$C_{12}$ alkyl or substituted $C_1$-$C_{12}$ alkyl.
11. The compound of claim 1 wherein each of $R_1$, $R_4$ and $R_5$ are H.
12. The compound of claim 1 wherein $Q_1$ is azido or cyano.
13. The compound of claim 1 having the configuration:

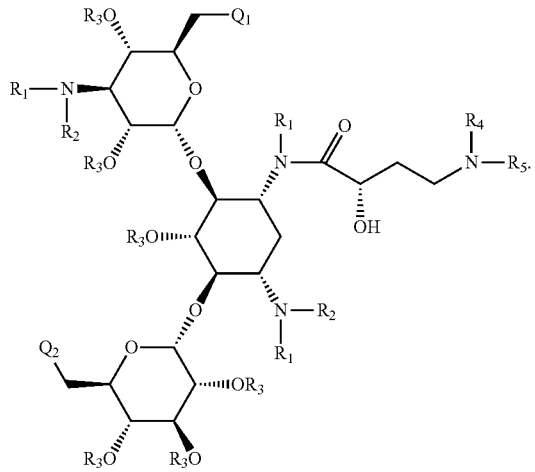

14. A method of treating a bacterial infection in a mammal in need thereof, comprising administering to said mammal an effective amount of a compound of claim 1.

* * * * *